US011962113B2

(12) United States Patent
Patil et al.

(10) Patent No.: US 11,962,113 B2
(45) Date of Patent: Apr. 16, 2024

(54) ELECTRONIC VAPING DEVICE AND CONNECTOR ASSEMBLY

(71) Applicant: Altria Client Services LLC, Richmond, VA (US)

(72) Inventors: Bipin Patil, Richmond, VA (US); Sean Sundberg, Richmond, VA (US); Kelli McKenna, Richmond, VA (US); Rangaraj Sundar, Richmond, VA (US); Greg Nelson, Richmond, VA (US); David Bennett, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 319 days.

(21) Appl. No.: 17/403,274

(22) Filed: Aug. 16, 2021

(65) Prior Publication Data
US 2021/0376542 A1    Dec. 2, 2021

Related U.S. Application Data

(62) Division of application No. 15/349,377, filed on Nov. 11, 2016, now Pat. No. 11,245,235.

(51) Int. Cl.
*H01R 24/38*    (2011.01)
*A24F 40/40*    (2020.01)
(Continued)

(52) U.S. Cl.
CPC ............ *H01R 24/38* (2013.01); *A24F 40/40* (2020.01); *A24F 40/42* (2020.01); *A24F 40/46* (2020.01);
(Continued)

(58) Field of Classification Search
None
See application file for complete search history.

(56) References Cited

U.S. PATENT DOCUMENTS

| 9,289,014 B2 | 3/2016 | Tucker et al. |
| 2013/0119151 A1 | 5/2013 | Moran et al. |
| (Continued) | | |

FOREIGN PATENT DOCUMENTS

| CN | 203058297 U | 7/2013 |
| CN | 203341009 U | 12/2013 |
| (Continued) | | |

OTHER PUBLICATIONS

International Search Report and Written Opinion for corresponding International Application No. PCT/EP2017/078961 dated Mar. 1, 2018.
(Continued)

*Primary Examiner* — John J Norton
(74) *Attorney, Agent, or Firm* — Harness, Dickey & Pierce, P.L.C.

(57) ABSTRACT

A connector assembly of a cartridge of an electronic vaping device may be formed by metal in-molding. The connector assembly may include a connector body that is integrally formed. The connector body may include a base portion that is generally cylindrical, a nose portion extending from a first end of the base portion, and at least two slots extending longitudinally through the base portion and on opposing sides of the nose portion. An electrical lead extends through each of the at least two slots.

14 Claims, 6 Drawing Sheets

(51) Int. Cl.
  *A24F 40/42* (2020.01)
  *A24F 40/46* (2020.01)
  *A24F 40/70* (2020.01)
  *A61M 15/06* (2006.01)
  *H01R 13/03* (2006.01)
  *H05B 1/02* (2006.01)

(52) U.S. Cl.
  CPC ............. *A24F 40/70* (2020.01); *A61M 15/06* (2013.01); *H05B 1/0244* (2013.01); *H01R 13/03* (2013.01); *H05B 2203/021* (2013.01)

(56) References Cited

U.S. PATENT DOCUMENTS

| | | |
|---|---|---|
| 2013/0192623 A1 | 8/2013 | Tucker et al. |
| 2013/0255675 A1 | 10/2013 | Liu |
| 2014/0224244 A1 | 8/2014 | Liu |
| 2014/0261408 A1 | 9/2014 | DePiano et al. |
| 2015/0013701 A1 | 1/2015 | Liu |
| 2015/0020823 A1 | 1/2015 | Lipowicz et al. |
| 2015/0027461 A1 | 1/2015 | Liu |
| 2015/0027463 A1 | 1/2015 | Liu |
| 2015/0053218 A1 | 2/2015 | Liu |
| 2015/0181944 A1 | 7/2015 | Li et al. |
| 2015/0196059 A1 | 7/2015 | Liu |
| 2015/0313275 A1 | 11/2015 | Anderson et al. |
| 2015/0335071 A1* | 11/2015 | Brinkley ............. H05B 1/0297 392/390 |
| 2016/0235119 A1 | 8/2016 | Liu |
| 2016/0309785 A1 | 10/2016 | Holtz |
| 2016/0309786 A1 | 10/2016 | Holtz et al. |
| 2016/0309788 A1 | 10/2016 | Hawes et al. |
| 2016/0324216 A1 | 11/2016 | Li et al. |

FOREIGN PATENT DOCUMENTS

| | | |
|---|---|---|
| CN | 103584287 A | 2/2014 |
| CN | 203618783 U | 6/2014 |
| CN | 204146338 U | 2/2015 |
| CN | 204169060 U | 2/2015 |
| CN | 106102491 A | 11/2016 |
| EP | 2888964 A1 | 7/2015 |
| EP | 2946678 A1 | 11/2015 |
| JP | H09280467 A | 10/1997 |
| JP | 200659991 A | 3/2006 |
| JP | 2014529996 A | 11/2014 |
| JP | 2015505476 A | 2/2015 |
| RU | 2372194 C2 | 11/2009 |
| WO | WO-2013159245 A1 | 10/2013 |
| WO | WO-2015/078147 A1 | 6/2015 |
| WO | WO-2016/023824 A1 | 2/2016 |
| WO | WO-2016/122417 A1 | 8/2016 |

OTHER PUBLICATIONS

Chinese First Office Action for corresponding Application No. 201780064361.4, dated Aug. 4, 2021, with English translation.
Japanese Decision to Grant for corresponding Application No. 2019-524373, dated May 16, 2022, with English translation.
Japanese Notification of Reasons for Refusal for corresponding Application No. 2019-524373, dated Nov. 15, 2021, with English Translation.
Russian Notice of Allowance for Corresponding Application No. 2019117381, dated Oct. 4, 2021, English translation included.
Korean Notice of Allowance for Application No. 10-2019-7010550, dated May 15, 2023, and English Translation included.

* cited by examiner

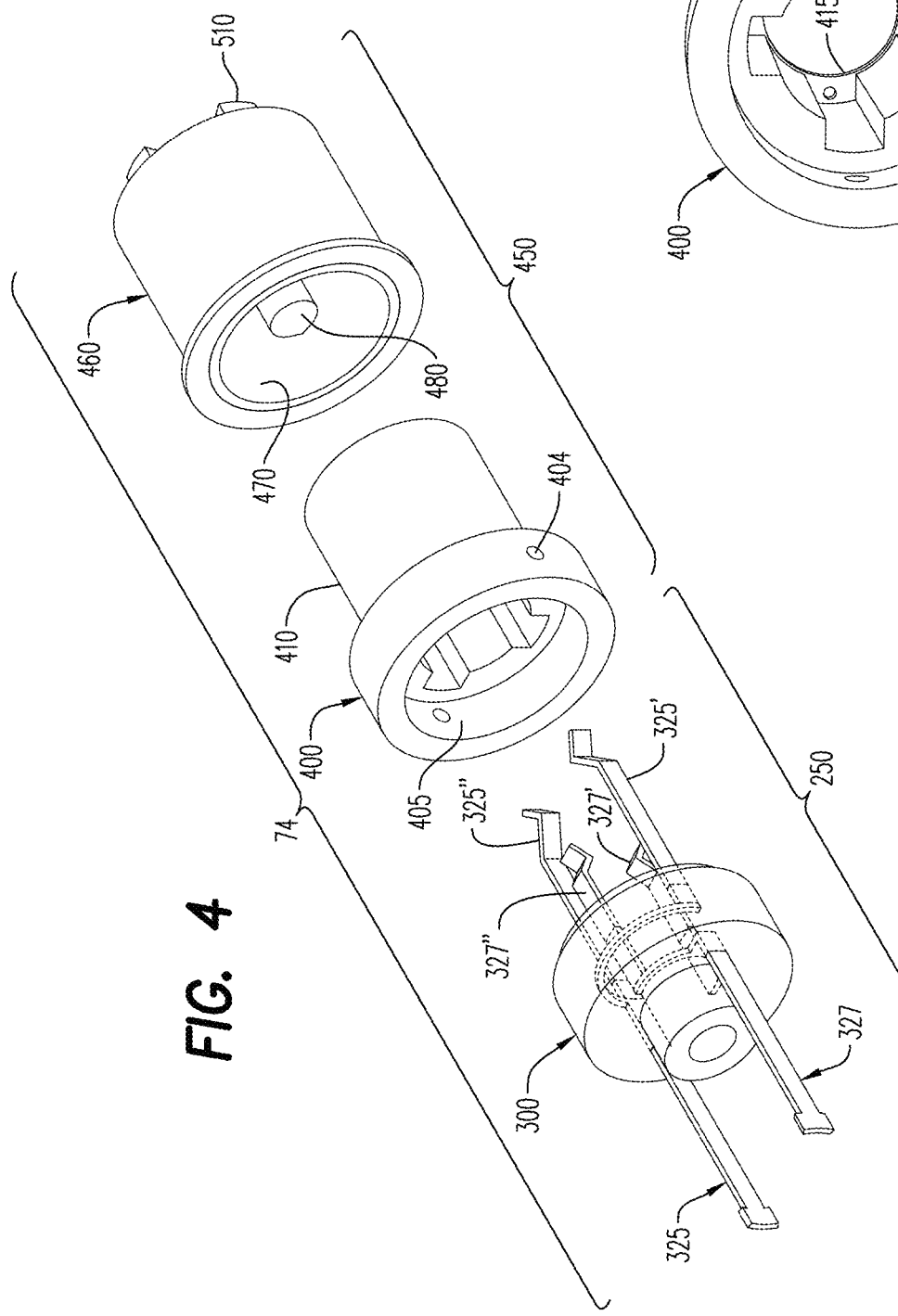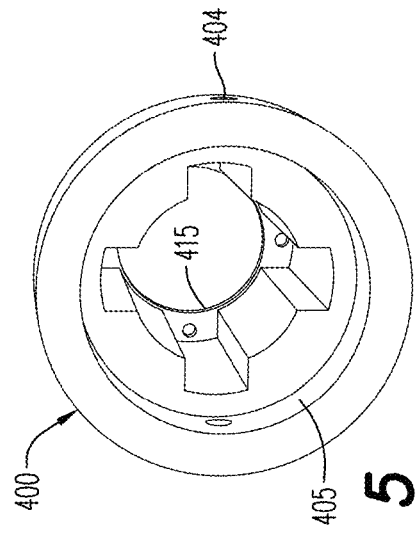

ELECTRONIC VAPING DEVICE AND CONNECTOR ASSEMBLY

CROSS-REFERENCE TO RELATED APPLICATIONS

This application is a divisional application of U.S. application Ser. No. 15/349,377 filed on Nov. 11, 2016, the entire contents of which are hereby incorporated by reference.

BACKGROUND

Field

The present disclosure relates to a connector assembly of an electronic vaping or e-vaping device and methods of forming the connector assembly.

Description of Related Art

Electronic vaping devices may include a power supply section and a cartridge. The power supply section and the cartridge may be connected by a connector, such as a threaded connector.

SUMMARY

At least one example embodiment relates to a connector assembly of a cartridge of an electronic vaping device.

In at least one example embodiment, a connector assembly of a cartridge of an electronic vaping device includes: a first connector body, a second connector body, and at least two electrical leads, each including a first end and a second end. The first connector body includes a first base portion that is generally cylindrical, a nose portion extending from a first end of the first base portion, at least two slots extending longitudinally through the first base portion and on opposing sides of the nose portion; and a first orifice extending longitudinally through the first base portion and the nose portion. The nose portion is generally cylindrical. The nose portion has a smaller diameter than the first base portion. The first end of each of the electrical leads extends through a respective one of the at least two slots. The second connector body includes a second base portion that is generally cylindrical, a tubular portion extending longitudinally from a second end of the second base portion; and a second orifice extending through the second base portion and the tubular portion. The second orifice is configured to receive a portion of the first base portion of the first connector body and the second end of each of the at least two electrical leads, such that the second end of each of the at least two electrical leads abuts an inner surface of the second orifice.

In at least one example embodiment, the at least two electrical leads are formed of stainless steel. The at least two electrical leads may have a cross-sectional area sufficient to reduce an electrical resistance of the leads.

In at least one example embodiment, the connector assembly may also include a third slot extending longitudinally through the base portion, a third electrical lead extending through the third slot, a fourth slot extending longitudinally through the base portion, and a fourth electrical lead extending through the fourth slot.

In at least one example embodiment, each of the first the connector body and the second connector body is formed of at least one polymer.

In at least one example embodiment, the at least two electrical leads include a generally U-shaped notch at the second end thereof.

In at least one example embodiment, the connector assembly may also include an air inlet in the second base portion of the second connector body. The air inlet may be in fluid communication with the first orifice in the first connector piece.

At least one example embodiment relates to a cartridge of an electronic vaping device.

In at least one example embodiment, a cartridge of an electronic vaping device includes a housing extending in a longitudinal direction, the housing having a first end and a second end, an inner tube coaxially positioned in the housing, a heating element in the housing, and a connector assembly. The connector assembly may include a first connector body, a second connector body, and at least two electrical leads each including a first end and a second end. The first connector body includes a first base portion that is generally cylindrical, a nose portion extending from a first end of the first base portion, at least two slots extending longitudinally through the first base portion and on opposing sides of the nose portion; and a first orifice extending longitudinally through the first base portion and the nose portion. The nose portion is generally cylindrical. The nose portion has a smaller diameter than the first base portion. The first end of each of the electrical leads extends through a respective one of the at least two slots. The second connector body includes a second base portion that is generally cylindrical, a tubular portion extending longitudinally from a second end of the second base portion; and a second orifice extending through the second base portion and the tubular portion. The second orifice is configured to receive a portion of the first base portion of the first connector body and the second end of each of the at least two electrical leads, such that the second end of each of the at least two electrical leads abuts an inner surface of the second orifice.

In at least one example embodiment, the at least two electrical leads are formed of stainless steel. The at least two electrical leads may have a cross-sectional area sufficient to reduce an electrical resistance of the leads.

In at least one example embodiment, the connector assembly may also include a third slot extending longitudinally through the base portion, a third electrical lead extending through the third slot, a fourth slot extending longitudinally through the base portion, and a fourth electrical lead extending through the fourth slot.

In at least one example embodiment, each of the first the connector body and the second connector body is formed of at least one polymer.

In at least one example embodiment, the at least two electrical leads include a generally U-shaped notch at the second end thereof.

In at least one example embodiment, the connector assembly may also include an air inlet in the second base portion of the second connector body. The air inlet may be in fluid communication with the first orifice in the first connector piece.

In at least one example embodiment, the cartridge may also include a microprocessor configured to control temperature of a heater. The microprocessor may be in the housing.

At least one example embodiment relates to an electronic vaping device.

In at least one example embodiment, an electronic vaping device includes a cartridge and a power supply section. In at least one example embodiment, the cartridge includes a housing extending in a longitudinal direction, the housing having a first end and a second end, an inner tube coaxially positioned in the housing, a heating element in the housing, and a connector assembly. The connector assembly may include a first connector body, a second connector body, and at least two electrical leads each including a first end and a second end. The first connector body includes a first base portion that is generally cylindrical, a nose portion extending from a first end of the first base portion, at least two slots extending longitudinally through the first base portion and on opposing sides of the nose portion; and a first orifice extending longitudinally through the first base portion and the nose portion. The nose portion is generally cylindrical. The nose portion has a smaller diameter than the first base portion. The first end of each of the electrical leads extends through a respective one of the at least two slots. The second connector body includes a second base portion that is generally cylindrical, a tubular portion extending longitudinally from a second end of the second base portion; and a second orifice extending through the second base portion and the tubular portion. The second orifice is configured to receive a portion of the first base portion of the first connector body and the second end of each of the at least two electrical leads, such that the second end of each of the at least two electrical leads abuts an inner surface of the second orifice. The power supply section may include a second housing, a battery in the housing, and electrical contacts configured to electrically connect the battery to the heater when the cartridge is connected to the power supply section.

In at least one example embodiment, the electrical contacts are formed of at least one of copper coated with tin and brass alloys.

In at least one example embodiment, the electronic vaping device may include a second connector assembly arranged in a first end of the second housing. The second connector assembly may include a generally cup-shaped connector piece and a metal lining, the connector piece and the metal lining configured to receive the tubular portion of the second connector body.

In at least one example embodiment, the second connector body may include a post extending through a bottom of the connector piece, the electrical leads configured to be received between the metal lining and the post.

At least one example embodiment relates to a method of making a connector assembly.

In at least one example embodiment, a method of making a connector assembly of a cartridge of an electronic vaping device may include metal insert molding the connector assembly.

In at least one example embodiment, the connector assembly may include a first connector body, a second connector body, and at least two electrical leads each including a first end and a second end. The first connector body includes a first base portion that is generally cylindrical, a nose portion extending from a first end of the first base portion, at least two slots extending longitudinally through the first base portion and on opposing sides of the nose portion; and a first orifice extending longitudinally through the first base portion and the nose portion. The nose portion is generally cylindrical. The nose portion has a smaller diameter than the first base portion. The first end of each of the electrical leads extends through a respective one of the at least two slots. The second connector body includes a second base portion that is generally cylindrical, a tubular portion extending longitudinally from a second end of the second base portion; and a second orifice extending through the second base portion and the tubular portion. The second orifice is configured to receive a portion of the first base portion of the first connector body and the second end of each of the at least two electrical leads, such that the second end of each of the at least two electrical leads abuts an inner surface of the second orifice.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 4 is an exploded view of the connector of FIGS. 1-3 according to at least one example embodiment.

FIG. 5 is a first end view of a second connector body of the connector of FIGS. 1-4 according to at least one example embodiment.

DETAILED DESCRIPTION OF EXAMPLE EMBODIMENTS

Figure 1:
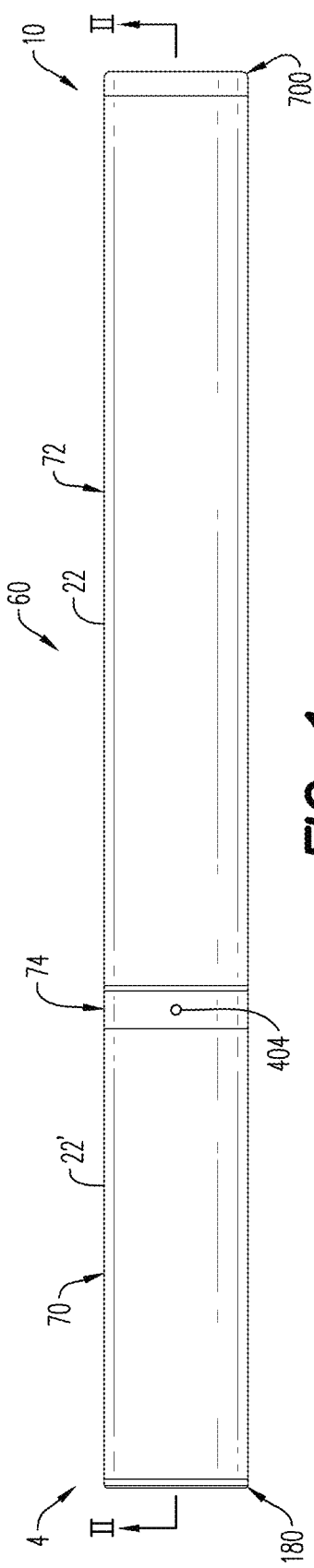
FIG. 1 is a side view of an electronic vaping device including a connector according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

At least one example embodiment relates to an electronic vaping device.

In at least one example embodiment, as shown in FIG. 1, an electronic vaping device 60 may include a first section (or cartridge) 70 and a second section (or battery section) 72, which may be coupled together at a connector 74. The connector 74 may include a first connector assembly 250 (shown in FIG. 3) associated with the first section 70 and a second connector assembly 450 (shown in FIG. 3) associated with the second section. At least some portions of the first connector assembly may be formed by a metal in-molding process as described herein.

In at least one example embodiment, at least one air inlet 404 may extend through a portion of the connector 74. In at least one example embodiment, the air inlets 404 may be sized and configured such that the e-vaping device 60 has a resistance-to-draw (RTD) in the range of from about 60 mm $H_2O$ to about 150 mm $H_2O$.

In at least one example embodiment, the first section 70 may include a first housing 22' extending in a longitudinal direction, and the second section 72 may include a second housing 22 extending in the longitudinal direction. The electronic vaping device 60 includes a mouth-end insert 180 at a first end 4.

In at least one example embodiment, the first housing 22' and the second housing 22 may have a generally cylindrical cross-section. In other example embodiments, the housings 22, 22' may have a generally triangular cross-section along one or more of the first section 70 and the second section 72. Furthermore, the housings 22, 22' may have the same or different cross-section shape, or the same or different size. As discussed herein, the housings 22, 22' may also be referred to as outer or main housings.

In at least one example embodiment, the electronic vaping device 60 may include an end cap 700 at a second end 10 of the electronic vaping device 60.

Figure 2:
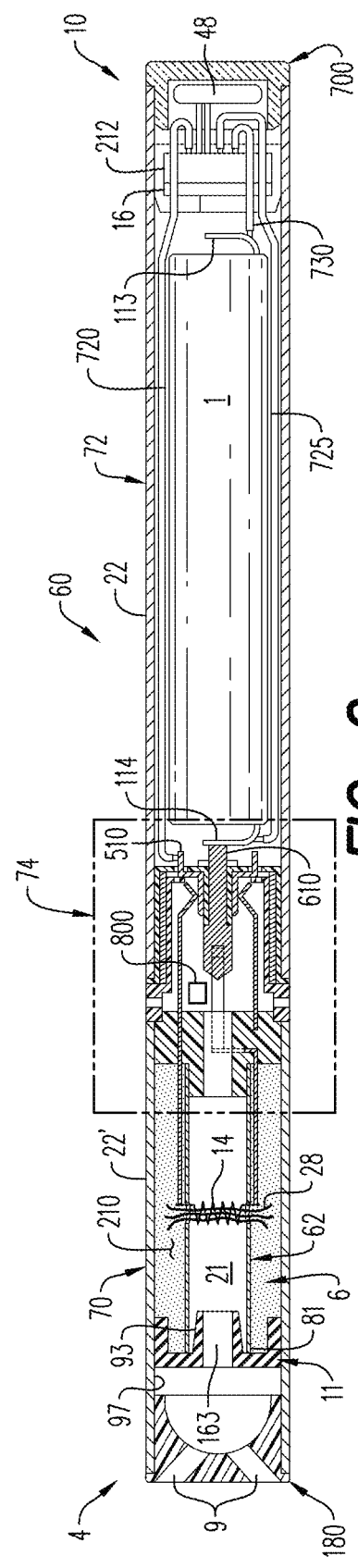
FIG. 2 is a cross-sectional view along line II-II of the electronic vaping device and the connector of FIG. 1 according to at least one example embodiment.

FIG. 2 is a cross-sectional view along line II-II of the electronic vaping device and connector of FIG. 1 according to at least one example embodiment.

In at least one example embodiment, as shown in FIG. 2, the electronic vaping device 60 may include a connector 74, which is shown in greater detail in FIGS. 3-6, which are described below.

In at least one example embodiment, as shown in FIG. 2, the first section 70 includes a reservoir 6 configured to store a pre-vapor formulation and a heater 14 that may vaporize the pre-vapor formulation to form a vapor. The e-vaping device 60 may also include the features set forth in U.S. Patent Application Publication No. 2013/0192623 to Tucker et al. filed Jan. 31, 2013 and/or features set forth in U.S. patent application Ser. No. 15/135,930 to Holtz et al. filed Apr. 22, 2016, the entire contents of each of which are incorporated herein by reference thereto. In other example embodiments, the e-vaping device may include the features set forth in U.S. patent application Ser. No. 15/135,923 filed Apr. 22, 2016, and/or U.S. Pat. No. 9,289,014 issued Mar. 22, 2016, the entire contents of each of which is incorporated herein by this reference thereto.

In at least one example embodiment, the reservoir 6 is established between the first housing 22' and an inner tube 62 of the first section 70. The inner tube 62 is positioned coaxially within the first housing 22'.

In at least one example embodiment, the reservoir 6 may at least partially surround a central inner passage 21 extending through the inner tube 62. The heater 14 may extend generally transversely across the inner passage between opposing portions of the reservoir 6. In some example embodiments, the heater 14 may extend generally parallel to a longitudinal axis of the inner passage 21.

In at least one example embodiment, the reservoir 6 may be sized and configured to hold enough pre-vapor formulation such that the electronic vaping device 60 may be configured for vaping for at least about 200 seconds.

In at least one example embodiment, the pre-vapor formulation may be a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, tobacco material, and/or vapor formers such as glycerin and propylene glycol. The pre-vapor formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

In at least one example embodiment, a storage medium 210 may be in the reservoir 6 between the first housing 22' and the inner tube 62. The storage medium 210 is configured to store the pre-vapor formulation therein. The storage medium 210 may include a winding of cotton gauze or other fibrous material about the inner tube 62.

In at least one example embodiment, the use of storage medium 210 negates a need for a gasket between the reservoir 6 and the first connector assembly 250. Gaskets may be formed of silicon or other materials, which may leach flavor from pre-vapor formulations. Thus, the removal of a second gasket from an electronic vaping device 60 aids in maintaining flavor and/or prolonging shelf-life of the pre-vapor formulation stored in the reservoir 6.

In at least one example embodiment, the storage medium 210 may be any porous and/or fibrous material that may hold the pre-vapor formulation therein. The storage medium 210 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium 210 may be a sintered, porous or foamed material. Also, the fibers may be sized to be irrespirable and may have a cross-section which has a Y-shape, cross shape, clover shape or any other suitable shape.

In at least one example embodiment, as shown in FIG. 2, the first section 70 also includes the heating element 14 that may vaporize the pre-vapor formulation, which may be drawn from the reservoir 6 by a wick 28. Ends of the heating element 14 and the wick 28 may extend through holes or slots in the inner tube 62, and into the reservoir 6.

In at least one example embodiment, as shown in FIG. 2, a gasket 11 is fitted into a first end portion 81 of the inner tube 62 so as to reduce leakage from the reservoir via the first end 4 of the electronic vaping device 60. The gasket 11 includes a nose portion 93 that may be fitted into the first end portion 81 of the inner tube 62. An outer perimeter of the gasket 11 provides a substantially liquid-tight seal with an interior surface 97 of the first housing 22'. The gasket 11 includes a central channel 163 disposed between the inner passage 21 of the inner tube 62 and the mouth-end insert 180, which may transport the vapor from the inner passage 21 to the mouth-end insert 180.

During vaping, pre-vapor formulation is transferred from the reservoir 6 to the proximity of the heating element 14 by the wick 28. The wick 28 may include a first end portion and a second end portion, which may extend into opposite sides of the reservoir 6. The heating element 14 may at least partially surround a central portion of the wick 28 such that when the heating element 14 is activated, the pre-vapor formulation in the central portion of the wick 28 is vaporized by the heating element 14 to form a vapor.

In at least one example embodiment, the wick 28 includes filaments (or threads) having a capacity to draw the pre-vapor formulation. For example, the wick 28 may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the electronic vaping device 60. In at least one example embodiment, the wick 28 may include one to eight filament strands, each strand comprising a plurality of glass filaments twisted together. The end portions of the wick 28 may be flexible and foldable into the confines of the reservoir 6. The filaments may have a cross-section that is generally cross-shaped, clover-shaped, Y-shaped, or in any other suitable shape.

In at least one example embodiment, the wick 28 may include any suitable material or combination of materials. Examples of suitable materials may be, but not limited to, glass, ceramic- or graphite-based materials. The wick 28 may have any suitable capillarity drawing action to accommodate pre-vapor formulations having different physical properties such as density, viscosity, surface tension and vapor pressure.

In at least one example embodiment, as shown in FIG. 2, the heating element 14 may include a wire coil which at least partially surrounds the wick 28. The wire may be a metal wire and/or the heating element coil may extend fully or partially along the length of the wick 28. The heating element coil may further extend fully or partially around the circumference of the wick 28. In some example embodiments, the heating element coil 14 may or may not be in contact with the wick 28.

The heating element 14 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 14 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 14 may include at least one material selected from the group consisting of stainless steel, copper, copper alloys, nickel-chromium alloys, super alloys and combinations thereof. In an example embodiment, the heating element 14 may be formed of nickel-chromium alloys or iron-chromium alloys. In another example embodiment, the heating element 14 may be a ceramic heating element having an electrically resistive layer on an outside surface thereof.

In at least one example embodiment, the heating element 14 may heat pre-vapor formulation in the wick 28 by thermal conduction. Alternatively, heat from the heating element 14 may be conducted to the pre-vapor formulation by means of a heat conductive element or the heating element 14 may transfer heat to the incoming ambient air that is drawn through the electronic vaping device 60 during vaping, which in turn heats the pre-vapor formulation by convection.

Figure 3A:
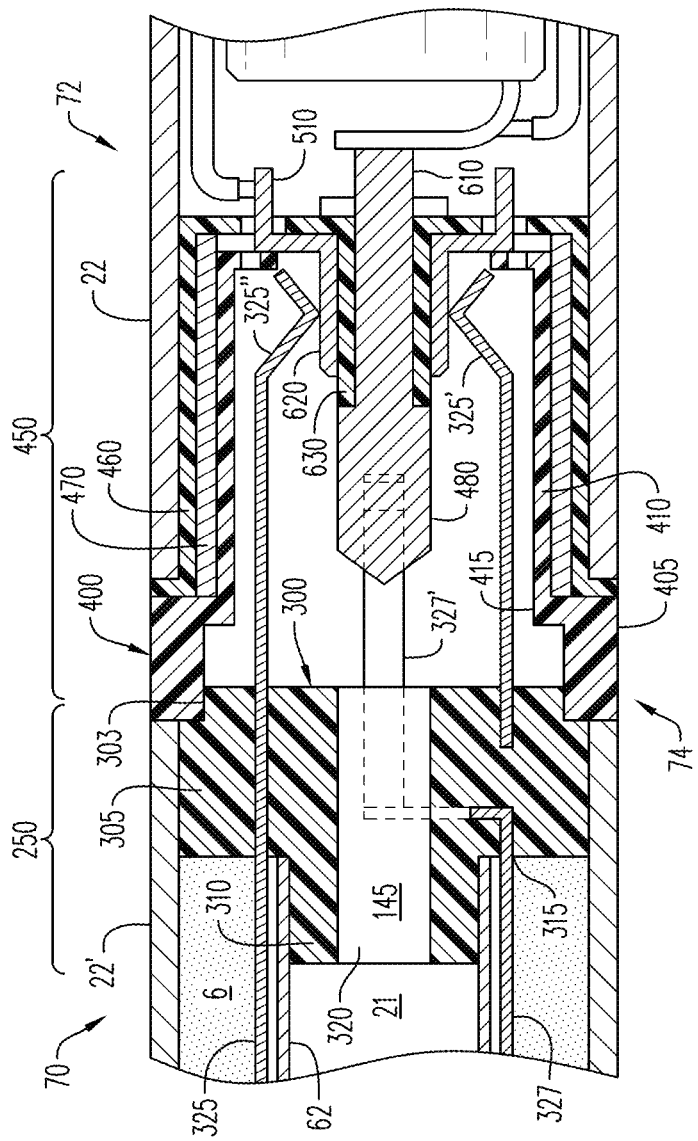
FIG. 3A is an enlarged view of the connector and a portion of the electronic vaping of FIGS. 1 and 2 according to at least one example embodiment.

In at least one example embodiment, as shown in FIG. 3A, electrical leads 325, 327 may extend from the heating element 14 and through the reservoir 6. The electrical leads 325, 327 may be welded to ends of the heating element 14 or attached to ends of the heating element 14 by crimping. In other example embodiments, the electrical leads 325, 327 may include a notch and/or be sized and configured to receive and hold ends of the heating element 14 in place without the need for welding and/or crimping. Thus, when the first section 70 first connector assembly 250 is connected with the second connector assembly 400 of the second section 72, an electrical connection may be formed between the power supply 1 in the second section 72 and the heating element 14 in the first section 70 as described herein. In at least one example embodiment, the electrical leads 325, 327 may be integrally formed with the heating element 14.

In at least one example embodiment, the electrical leads 325, 327 may be formed of copper or stainless steel. Stainless steel may be used to reduce reactions with the pre-vapor formulation when the electrical leads 325, 327 pass through the reservoir 6 or are otherwise in contact with the pre-vapor formulation.

It should be appreciated that, instead of using a wick 28, the heating element 14 may be a porous material which incorporates a resistance heating element formed of a material having a high electrical resistance capable of generating heat quickly.

In at least one example embodiment, the mouth-end insert 180 may be received in the first housing 22' at the first end 4. The mouth-end insert 180 may include two or more outlets 9, which may be diverging outlets. The outlets 9 may be angled outwardly in relation to the longitudinal axis of the electronic vaping device 60. The outlets 9 may be substantially uniformly distributed about the perimeter of an end surface of the mouth-end insert 8.

In at least one example embodiment, as shown in FIG. 2, the second section 72 includes a power supply 1, a control circuit 212, and a sensor 16 configured to sense negative pressure and/or air being drawn into the electronic vaping device 60.

In at least one example embodiment, the power supply 1 includes a battery arranged in the electronic vaping device 60. The battery may be a Lithium-ion battery or one of its variants, for example a Lithium-ion polymer battery. Alternatively, the battery may be a nickel-metal hydride battery, a nickel cadmium battery, a lithium-manganese battery, a lithium-cobalt battery or a fuel cell. The electronic vaping device 60 may be vapable by an adult vaper until the energy in the power supply 1 is depleted or in the case of lithium polymer battery, a minimum voltage cut-off level is achieved.

In at least one example embodiment, the power supply 1 may be rechargeable and may include circuitry configured to allow the battery to be chargeable by an external charging device. To recharge the electronic vaping device 60, an USB charger or other suitable charger assembly may be used.

In at least one example embodiment, the sensor 16 is configured to generate an output indicative of a magnitude and direction of airflow in the electronic vaping device 60. The control circuit 212 receives the output of the sensor 16, and determines if (1) the direction of the airflow indicates a draw on the mouth-end insert 180 (versus blowing) and (2) the magnitude of the draw exceeds a threshold level. If these vaping conditions are met, the control circuit 212 electrically connects the power supply 1 to the heating element 14; thus, activating the heating element 14. Namely, the control circuit 12 electrically connects to the first and second leads 325, 327 (e.g., by activating a heating element power control transistor forming part of the control circuit 212) such that the heating element 14 becomes electrically connected to the power supply 1. In an alternative embodiment, the sensor 16 may indicate a pressure drop, and the control circuit 212 activates the heating element 14 in response thereto.

In at least one example embodiment, the control circuit 212 may also include a light 48, which the control circuit 212 activates to glow when the heating element 14 is activated and/or the battery 1 is recharged. The light 48 may include one or more light-emitting diodes (LEDs). The LEDs may include one or more colors (e.g., white, yellow, red, green, blue, etc.). Moreover, the light 48 may be arranged to be visible to an adult vaper during vaping, and may be positioned between the first end 4 and the second end 10 of the electronic vaping device 60. In addition, the light 48 may be utilized for e-vaping system diagnostics or to indicate that recharging is in progress. The light 48 may also be configured such that the adult vaper may activate and/or deactivate the activation light 48 for privacy.

In at least one example embodiment, the control circuit 212 may include a time-period limiter. In another example embodiment, the control circuit 12 may include a manually operable switch for an adult vaper to initiate heating. The time-period of the electric current supply to the heating element 14 may be set or pre-set depending on the amount of pre-vapor formulation desired to be vaporized.

Next, operation of the electronic vaping device 60 to create a vapor will be described. For example, air is drawn primarily into the first section 70 through the at least one air inlet 404 in response to a draw on the mouth-end insert 180. The air passes through the air inlet 404, into the central channel 21 of inner tube 62, and through the outlet 9 of the mouth-end insert 180. If the control circuit 212 detects the vaping conditions discussed above, the control circuit 212 initiates power supply to the heating element 14, such that the heating element 14 heats pre-vapor formulation in the wick 28. The vapor and air flowing through the inner passage 21 combine and exit the electronic vaping device 60 via the outlet 9 of the mouth-end insert 180.

When activated, the heating element 14 may heat a portion of the wick 28 for less than about 10 seconds.

In at least one example embodiment, the first section 70 may be replaceable. In other words, once the pre-vapor formulation of the cartridge is depleted, only the first section 70 may be replaced. An alternate arrangement may include an example embodiment where the entire electronic vaping device 60 may be disposed once the reservoir 6 is depleted. In at least one example embodiment, the electronic vaping device 60 may be a one-piece e-vaping device having a single outer housing.

In at least one example embodiment, the electronic vaping device 60 may be about 80 mm to about 110 mm long and about 7 mm to about 8 mm in diameter. For example, in one example embodiment, the electronic vaping device 60 may be about 84 mm long and may have a diameter of about 7.8 mm.

FIG. 3A is an enlarged view of the connector and a portion of the electronic vaping of FIGS. 1 and 2 according to at least one example embodiment.

In at least one example embodiment, as shown in FIG. 3A, the connector 74 includes a first connector assembly 250 and a second connector assembly 450. The first connector assembly 250 is arranged in the first section 70 and the second connector assembly 450 is arranged in the second section 72. The first connector assembly 250 is removably connectable to the second connector assembly 450 to join the first section 70 with the second section 72.

In at least one example embodiment, the first connector assembly 250 includes a first connector body 300 and a second connector body 400.

In at least one example embodiment, as shown in FIG. 3A, the first connector body 300 includes a first base portion 305 and a nose portion 310 extending from the first base portion 305. The nose portion 310 may be sized and configured to fit snugly within a second end of an inner tube 62. A first orifice 320 extends through the first base portion 305 and the nose portion 310 of the first connector body 300. The first orifice 320 establishes a flow passage 145 through which air may flow. The flow passage 145 is in fluid communication with the central air passage 21 in the inner tube 62.

In at least one example embodiment, the first orifice 320 has an inner diameter ranging from about 1.40 mm to about 1.80 mm (e.g., about 1.45 mm to about 1.75 mm or about 1.50 mm to about 1.70 mm). For example, the inner diameter may be about 1.60 mm, and the inner diameter may aid in establishing a desired resistance-to-draw (RTD) ranging from about 90 mm $H_2O$ to about 120 mm $H_2O$. The inner diameter of the first orifice 320 may be altered to adjust the RTD of the electronic vaping device 60.

In at least one example embodiment, the second connector body 400 includes a second base portion 405 and a tubular portion 410.

In at least one example embodiment, the tubular portion 410 extends longitudinally from the second base portion 405 towards the second end 10 of the electronic vaping device 60. A second orifice 415 extends through the tubular portion 410 and the second base portion 405. The second orifice 415 may have a generally cylindrical cross-section. The second connector body 400 is generally T-shaped when viewed form a side.

In at least one example embodiment, the first base portion 305 of the first connector body 300 includes a collar portion 303 extending from the first base portion 305 in the longitudinal direction towards the second end 10 of the electronic vaping device 60. The collar portion 303 may be generally cylindrical and may have a smaller outer diameter than the first base portion 305. The collar portion 303 may be received within the second base portion 405 of the second connector body 400, such that the second base portion 405 abuts the larger portion of the first base portion 305.

In at least one example embodiment, the second base portion 405 may have an outer diameter that is substantially the same as an outer diameter of the first housing 22', and an inner diameter that is substantially the same as an outer diameter of the portion of the first base portion 305 that is received in the second base portion 405.

In at least one example embodiment, the electrical leads 325, 327 extend through the slots 315 in the first base portion 305 such that one of the electrical leads 325, 327 is on each side of the nose portion 310 of the first connector body 300. A first end of each of the electrical leads 325, 327 is configured to contact and/or attach to opposing ends of the heating element 14. A second end of each of the electrical leads 325, 327 may be received in the tubular portion 410 of the second connector body 400. The electrical leads 325, 327 may be biased so that the second end of each of the electrical leads 325, 327 abuts an inner surface of the tubular portion 410. Central portions of the electrical leads 325, 327 are in-molded within the first connector body 300, such that the electrical lead 325 is electrically insulated from the electrical lead 327. The slots 315 may vary in shape, such that the leads 325, 327 extend longitudinally and transversely through the first connector body 300.

The at least two electrical leads 325, 327 may be formed of stainless steel. The stainless steel may be subjected to a passivation treatment and/or may be coated with a chemical vapor deposited poly(p-xylylene) polymer coating, such as a Parylene coating, which is a chemical vapor deposited poly(p-xylylene) polymer. The electrical leads 325, 327 pass through the first connector body 300 and have portions extending therefrom. The electrical lead 325 has a longer portion extending from the first connector body 300 than the electrical lead 327.

In at least one example embodiment, the first connector body 300 and the second connector body 400 may be formed of a polymer. The polymer may include at least one of: cyclic olefin copolymer, such as TOPAS® 6013M-07, cyclo-olefin polymer, such as Zeon Chemical ZEONEX® 480R (Pharma Grade), copolyester, such as Eastman Tritan MX731, Eastman Tritan Tx1501HF (FDA Grade), Eastman Tritan Tx1501HF with colorant/UV additive package, or Eastman Tritan TX2001 (FDA Grade), high density polyethylene, polycarbonate, such as Bayer Makrolon® 2858, or polypropylene.

In at least one example embodiment, as shown in FIG. 3A, the first base portion 305 is generally cylindrical. In at least one example embodiment, the first base portion 305 has an outer diameter that is substantially the same as or less than an inner diameter of the first housing 22', such that the first base portion 305 aids in sealing the reservoir 6 established between the first housing 22' and the inner tube 62 without the need for an additional gasket, adhesive, or seal. The first base portion 305 may be held within the first housing 22' by friction fit.

In at least one example embodiment, when the first connector assembly 250 is arranged in the first section 70, the second connector body 400 abuts an edge of the first housing 22' and the tubular portion 410 of the second connector body 400 extends from the second end of the first housing 22'.

In at least one example embodiment, the second connector assembly 450 is arranged in the second section 72. The second connector assembly 450 may include a connector piece 460 that is generally cup-shaped. A lining 470 may be arranged on an inner surface of the connector piece 460. The lining 470 may be formed of metal. A post 480 may extend through a bottom portion of the connector piece 460. The post 480 is sized and configured to be received in the tubular portion 410 of the second connector body 400 of the first connector assembly 250. The connector piece 460 has an inner diameter that is about the same or larger than an outer diameter of the tubular portion 410, such that the tubular portion 410 is held within the connector piece 460 by friction fit. A pin 610 extends from the post 480 and through the connector piece 460.

In at least one example embodiment, additional electrical leads may also extend through the first connector assembly 250 so as to establish a connection between the power supply 1 and a microprocessor 800 (shown in FIG. 2) arranged in the first section 70. For example, the electronic vaping device 60 may include three contacts, which are configured to contact a conductive cylinder 620, the lining 407, and the post 480.

When the first connector assembly 250 and the second connector assembly 450 are joined, the electrical lead 325 contacts the conductive cylinder 620 that circumscribes the post 480 and the electrical lead 327 contacts the post 480 to establish an electrical connection between the heater 14 in the first section 70 and the a power supply 1 in the second section 72.

In at least one example embodiment, as shown in FIG. 3A, electrically conductive tabs 510 extend from the conductive cylinder 620, through the connector piece 460, and into the second section 72.

As shown in FIG. 3A, when the first connector assembly 250 is attached to the first section 70, at least a portion of the second base portion 405 and the tubular portion 410 protrude from the second end of the first housing 22'. In at least one example embodiment, the second connector assembly 450, when inserted in the outer housing 22 of the second section 72, may be flush with an edge of the second housing 22.

Figure 3B:
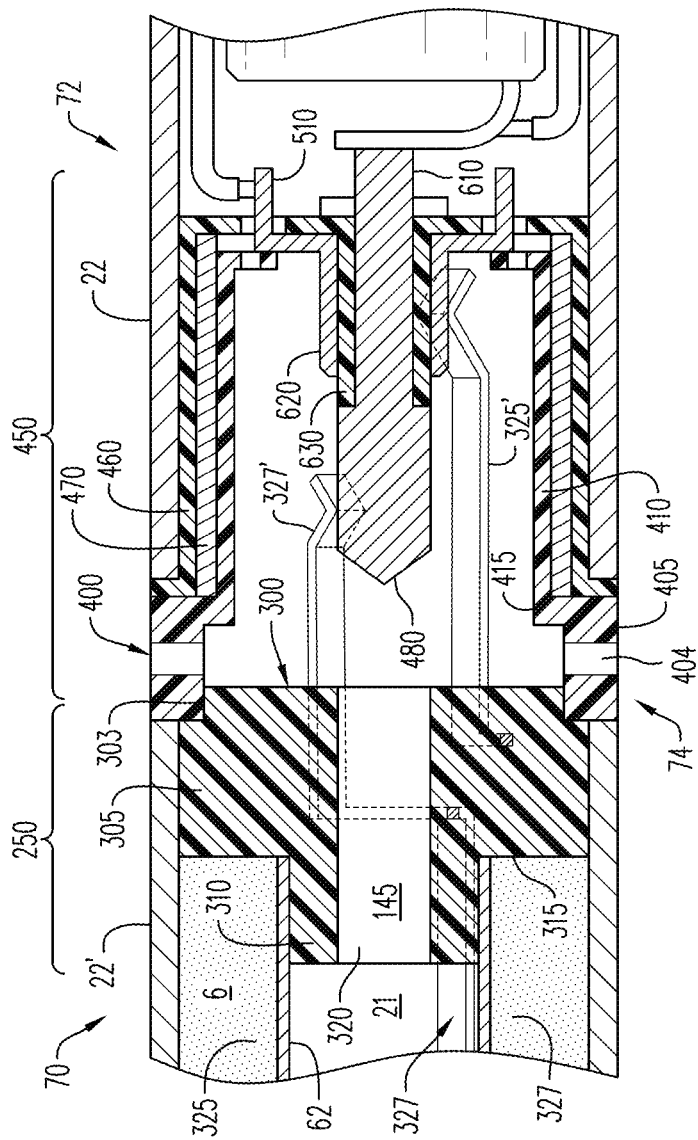
FIG. 3B is an enlarged cross-sectional view of the connector and a portion of the electronic vaping device of FIG. 3A with the cross-section rotated 45° with respect to the cross-section in FIG. 3A.

FIG. 3B is an enlarged cross-sectional view of the connector and a portion of the electronic vaping device of FIG. 3A with the cross-section rotated 45° with respect to the cross-section in FIG. 3A.

In at least one example embodiment, as shown in FIG. 3B, the connector is the same as in FIG. 3A, but is shown including at least one air inlet 404 that extends through the second base portion 405 in a direction that is substantially transverse to the longitudinal direction. The at least one air inlet 404 is in fluid communication with the flow passage 145.

Referring to FIGS. 2, 3A, and 3B, as shown, a first lead 720 electrically connects the electrically conductive tab 510 to the control circuit 212. A second lead 730 electrically connects the control circuit 212 to a first terminal 113 of the power supply 1. A third lead 725 electrically connects a second terminal 114 of the power supply 1 to the power terminal of the control circuit 212 to provide power to the control circuit 212. The second terminal 114 of the power supply 1 is also physically and electrically connected to the conductive pin 610. The conductive pin 610 may be formed of a conductive material (e.g., stainless steel, copper, etc). The conductive pin 610 nests within the insulator 630, and is electrically insulated from the conductive cylinder 620. When the first and second connector assemblies 250, 450 are mated, the lead 327 physically and electrically connects to the pin 610 via the lead portion 327', which contacts the post 480 (and lead portion 327", shown in FIG. 4). The lead 325 physically and electrically connects to the cylinder 620 and tab 510 via the lead portions 325', 325".

Figure 3D:
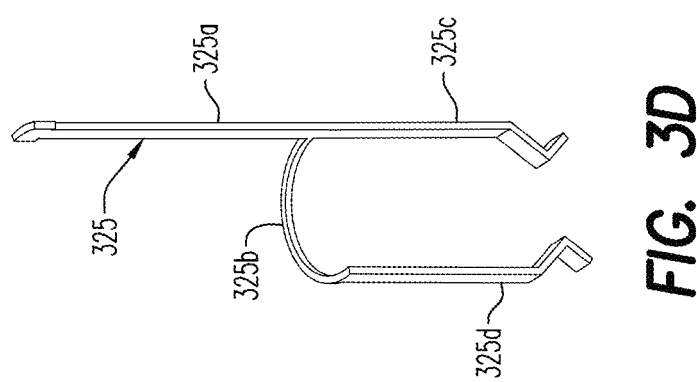
FIGS. 3C and 3D are enlarged perspective views of the electrical leads of the connector of FIGS. 3A and 3B.
Figure 3C:
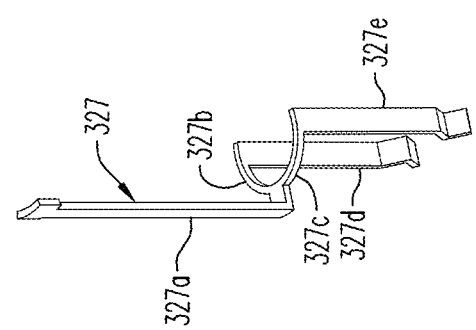

FIGS. 3C and 3D are enlarged perspective views of the electrical leads of the connector of FIGS. 3A and 3B.

In at least one example embodiment, as shown in FIG. 3C, the electrical lead 327 includes a first straight portion 327a, a first perpendicular portion 327b, a second perpendicular portion 327c, a second straight portion 327d, and a third straight portion 327e. The perpendicular portions 327b, 327c are in molded within the first connector body 300. The first straight portion 327a extends out of the first connector body 300 opposite the second straight portion 327d and the third straight portion 327e. The second straight portion 327d is positioned about 180° from the third straight portion 327e.

In other example embodiments, the electrical lead 327 may have other configurations including at least a portion that is in molded within the first connector body 300.

In at least one example embodiment, as shown in FIG. 3D, the electrical lead 325 includes a first straight portion 325a, a perpendicular portion 325b, and two leg portions 325c, 325d. The perpendicular portion 325b is in molded within the first connector body 300. The first straight portion and the two let portions extend from the first connector body 300. The first straight portion extends out of a first end of the first connector body 300, while the two leg portions extend from a second end of the first connector body 300.

In other example embodiments, the electrical lead 325 may have other configurations including at least a portion that is in molded within the first connector body 300.

FIG. 4 is an exploded view of the connector of FIGS. 1-3B according to at least one example embodiment.

In at least one example embodiment, as shown in FIG. 4, the first connector assembly 250 and the second connector assembly 450 are the same as in FIGS. 1-3B. As shown in FIG. 4, the electrical lead 325 includes two portions 325', 325", and the electrical lead 327 includes two portions 327', 327". The portions 325', 325" are longer than the portions 327', 327". In other example embodiments, the electrical lead 325 may include only one portion 325' and/or the electrical lead 327 may include only one portion 327'. More than one portion 325', 327' may be used to provide greater structural stability between the first connector body 300 and the second connector body 400. The lead portions 325', 325", 327', 327" may be substantially uniformly spaced about the first connector body 300 or non-uniformly spaced.

FIG. 5 is a first end view of a second connector body of the connector of FIGS. 1-4 according to at least one example embodiment.

In at least one example embodiment, as shown in FIG. 5, the second connector body 400 is the same as in FIGS. 1-4. As shown in FIG. 5, the second orifice 415 may have a generally cross-shaped cross-section such that each of the electrical lead portions 325', 325", 327', 327" may be held within respective arms of the cross-shaped second orifice 415.

Figure 6:
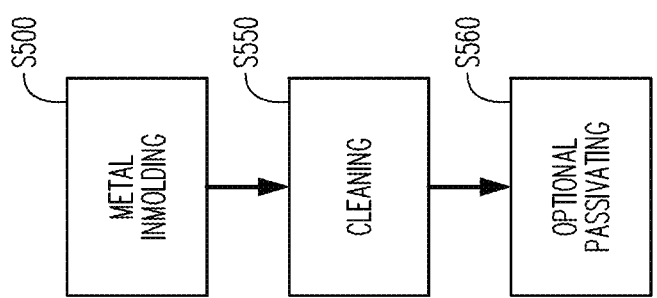
FIG. 6 is a flow chart illustrating a method of making a first connector assembly according to at least one example embodiment.

FIG. 6 is a flow chart illustrating a method of making a first connector assembly according to at least one example embodiment.

In at least one example embodiment, as shown in FIG. 6, a method of making the first and/or second connector assembly may include metal in-molding S500 electrical leads in a connector body. The electrical leads may be formed of stainless steel. The electrical leads and/or the connector assembly may be cleaned S550 before or after the in-molding operation. Following the cleaning S550, the leads and/or other metal components may undergo a passivation operation S560. The passivation operation S560 may occur after the cleaning operation S550, but before the metal in-molding operation S500 if desired.

In at least one example embodiment, as shown in FIG. 6, after in-molding, the electrical leads may be subjected to a cleaning and/or passivation operation to improve corrosion resistance of the post.

In at least one example embodiment, the passivation operation S650 may include a nitric acid treatment according to ASTM A 967 as set forth in Table 1 below.

TABLE 1

| Solution | Time | Temperature |
| --- | --- | --- |
| 20-25% nitric acid and 2.5% sodium dichromate | about 20 minutes | 120° F. to 130° F. |
| 20-40% nitric acid | about 30 minutes | 70° F. to 90° F. |
| 20-25% nitric acid | about 20 minutes | 120° F. to 140° F. |
| 45-55% nitric acid | about 30 minutes | 120° F. to 130° F. |

In at least one example embodiment, the passivation operation S650 may include a citric acid treatment according to ASTM A967 as set forth in Table 2 below.

TABLE 2

| Solution | Time | Temperature |
| --- | --- | --- |
| 4-10% citric acid | about 4 minutes | 140° F. to 160° F. |
| 4-10% citric acid | about 10 minutes | 120° F. to 140° F. |
| 4-1% citric acid | about 20 minutes | 70° F. to 120° F. |

Figure 7:
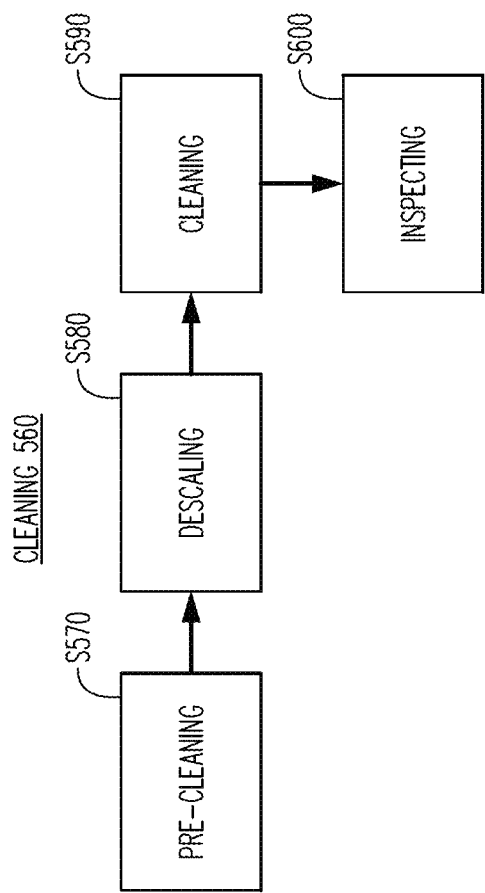
FIG. 7 is a flow chart illustrating the cleaning operation of FIG. 6 according to at least one example embodiment.

FIG. 7 is a flow chart illustrating the cleaning operation of FIG. 6 according to at least one example embodiment.

In at least one example embodiment, as shown in FIG. 7, the cleaning operation S560 may include a pre-cleaning operation S570, which may include cleaning the post with a solution and/or scrubbing the leads. The pre-cleaning may be done so that any passivation operations are uniformly applied to the leads. The pre-cleaning operation S570 may include any suitable cleaning process including an alkaline process, an emulsion process, a vapor degreasing process, an ultrasonic process, a detergent process, a chelate solution process, a mechanical process including one or more of abrasive blast, grinding, and/or wire brushing, a steam process, and/or a water jet process.

In at least one example embodiment, the cleaning operation S560 may include acid pickling and/or a mechanical descaling process. The cleaning operation S560 may also include acid cleaning to remove iron, light oxide films, and/or dirt from the post. Once the cleaning operation S560 is complete, the leads may be inspected S600.

In at least one example embodiment, is a descaling operation S580 and/or pickling process is performed, the process may be that described in ASTM A 380 Table A1, Part 1 titled "Acid Descaling." Before pickling, the surface must be pre-cleaned. Then, the descaling solution for an annealed austenitic stainless steel may be applied. The descaling solution may include about 8% to about 11% sulfuric acid. The descaling solution may be applied for about 5 minutes to about 45 minutes at a temperature of about 150° F. to about 180° F. Alternatively, the descaling solution may include about 15 to about 25% nitric acid and about 1 to about 8% hydrofluoric acid. This descaling solution may be applied to the post for about 5 minutes to about 30 minutes at a temperature ranging from about 70° F. to about 140° F. After the descaling and/or pickling process, the leads may be brushed with hot water and/or a high-pressure water jet until the wash water has a pH ranging from about 6 to about 8. Surfaces of the leads should then be inspected to ensure proper cleaning.

In at least one example embodiment, if the leads are formed of annealed 300 series stainless steel, the cleaning operation S560 may include acid cleaning, and the leads may be cleaned with a nitric-hydrofluoric acid according to ASTM A 380 Table A2, Part I: Cleaning with Nitric-hydrofluoric acid. The cleaning solution may include a solution including 6 to 25% nitric acid and 0.5 to 8% hydrofluoric acid. The cleaning may be done at a temperature ranging from about 70° F. to about 140° F. The acid cleaning may be done for as long as necessary to clean the leads.

In another example embodiment, the cleaning operation S560 of leads formed of an annealed, cold roller, thermally hardened, or work hardened 300 series stainless steel may include acid cleaning according to ASTM A 380 Table A2.1 Part II: Cleaning-passivation with Nitric Acid, which includes cleaning and passivation with nitric acid. A solution of 20% to 30% nitric acid is applied to the leads at a temperature of about 120° F. to about 160° F. for about 10 minutes to about 30 minutes. If a surface of the leads are shiny, the process may include applying a solution of about 20% to about 40% nitric acid and about 2% to about 6% sodium dichromate to the leads at a temperature of about 120° F. to about 160° F. for about 10 minutes to about 30 minutes.

In another example embodiment, if the leads are formed of 200 or 300 series stainless steel, the cleaning operation S560 may include acid cleaning according to ASTM A 380 Table A2.1 Part III: Cleaning with other chemical solutions. A solution of 1% citric acid and 1% sodium nitrate may be applied at about 70° F. for about 60 minutes. Alternatively, a solution of about 5% to about 10% ammonium citrate may be applied at a temperature ranging from about 120° F. to about 160° F. for about 10 minutes to about 60 minutes. In another embodiment, an inhibited ammonia-neutralized solution of ethylenediaminetetraacetic acid (EDTA) at a temperature of up to about 250° F. at a temperature of about 6 hours followed by hot water rinse.

In at least one example embodiment, following any of the acid washes, the surface of the leads should be rinsed until the rinse water has a pH ranging from about 6 to about 8.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A method of making a connector assembly of a cartridge of an electronic vaping device, the method comprising:
   metal insert molding the connector assembly,
   wherein the connector assembly comprises:
      a first connector body including,
         a first base portion that is generally cylindrical,
         a nose portion extending from a first end of the first base portion, the nose portion being generally cylindrical, and the nose portion having a smaller diameter than the first base portion,
         at least two slots extending longitudinally through the first base portion and on opposing sides of the nose portion, and
         a first orifice extending longitudinally through the first base portion and the nose portion;
      at least two electrical leads each including a first end and a second end, the first end of each of the electrical leads extending through a respective one of the at least two slots; and
      a second connector body including,
         a second base portion that is generally cylindrical,
         a tubular portion extending longitudinally from a second end of the second base portion, and
         a second orifice extending through the second base portion and the tubular portion, the second orifice configured to receive a portion of the first base portion of the first connector body and the second end of each of the at least two electrical leads, such that the second end of each of the at least two electrical leads abuts an inner surface of the second orifice.

2. The method of claim 1, wherein the electrical leads include stainless steel.

3. The method of claim 1, further comprising:
cleaning the connector assembly.

4. The method of claim 3, further comprising:
subjecting the electrical leads to a passivation process.

5. The method of claim 4, wherein the passivation process includes a nitric acid treatment.

6. The method of claim 4, wherein the passivation process includes a citric acid treatment.

7. The method of claim 3, wherein the cleaning includes a mechanical cleaning.

8. The method of claim 7, wherein the mechanical cleaning includes abrasive blasting.

9. The method of claim 7, wherein the mechanical cleaning includes grinding.

10. The method of claim 7, wherein the mechanical cleaning includes wire brushing.

11. The method of claim 7, wherein the mechanical cleaning includes abrasive blasting, grinding, wire brushing, or any combination thereof.

12. The method of claim 3, wherein the cleaning includes acid pickling.

13. The method of claim 3, wherein the cleaning includes mechanical descaling.

14. The method of claim 3, wherein the cleaning includes treating with hydrofluoric acid.

\* \* \* \* \*